(12) United States Patent
Benedict et al.

(10) Patent No.: US 10,792,403 B2
(45) Date of Patent: Oct. 6, 2020

(54) SUCTION SWAB FOR SURGICAL USE

(71) Applicant: ARTHREX, INC., Naples, FL (US)

(72) Inventors: Robert Benedict, Fort Meyers, FL (US); Brandon Roller, Naples, FL (US); James R. McWilliam, Rye, NY (US); Frank Grimaldi, Jr., Naples, FL (US); David Shepard, Naples, FL (US)

(73) Assignee: ARTHREX, INC., Naples, FL (US)

( * ) Notice: Subject to any disclaimer, the term of this patent is extended or adjusted under 35 U.S.C. 154(b) by 787 days.

(21) Appl. No.: 14/591,955

(22) Filed: Jan. 8, 2015

(65) Prior Publication Data

US 2016/0199549 A1     Jul. 14, 2016

(51) Int. Cl.
| | |
|---|---|
| *A61M 1/00* | (2006.01) |
| *A61M 27/00* | (2006.01) |
| *A61F 13/38* | (2006.01) |
| *A61M 35/00* | (2006.01) |
| *A61F 2/46* | (2006.01) |

(52) U.S. Cl.
CPC ............ *A61M 1/0084* (2013.01); *A61F 13/38* (2013.01); *A61M 27/00* (2013.01); *A61M 35/003* (2013.01); *A61F 2/4675* (2013.01); *A61M 2210/02* (2013.01)

(58) Field of Classification Search
CPC .. A61M 1/0084; A61M 27/00; A61M 35/003; A61M 2210/02; A61F 13/38; A61F 2002/4675; A61C 8/0006; A61C 8/0007; A61C 8/0092; A61C 17/0208
See application file for complete search history.

(56) References Cited

U.S. PATENT DOCUMENTS

| | | | | |
|---|---|---|---|---|
| 2,096,849 | A | * | 10/1937 | Felix .................. A47J 31/06 99/285 |
| 3,324,855 | A | * | 6/1967 | Heimlich .............. A61M 1/008 604/3 |
| 3,935,863 | A | * | 2/1976 | Kliger .................. A61F 13/38 604/369 |
| 5,151,094 | A | | 9/1992 | Hanifl |
| 5,921,972 | A | | 7/1999 | Skow |
| 7,845,944 | B2 | | 12/2010 | DiGasbarro |
| 8,246,948 | B2 | | 8/2012 | Swain |
| 8,398,398 | B1 | * | 3/2013 | Barham .............. A61C 17/043 433/91 |

(Continued)

FOREIGN PATENT DOCUMENTS

| | | | | |
|---|---|---|---|---|
| CA | 2499284 A1 | * | 8/2006 | ......... A61C 17/0208 |
| CA | 2499284 A1 | * | 8/2006 | ......... A61C 17/0208 |
| WO | 2014139707 A1 | | 9/2014 | |

OTHER PUBLICATIONS

Steadman, J. et al. "Microfracture: Its History and Experience of the Developing Surgeon" Cartilage 1 (2) 78-86 (2010).*

(Continued)

*Primary Examiner* — Nicholas J. Weiss
*Assistant Examiner* — Gabriella E Burnette
(74) *Attorney, Agent, or Firm* — Carlson, Gaskey & Olds

(57) ABSTRACT

A surgical method according to an exemplary aspect of the present disclosure includes, among other things, drying an osteochondral defect using a suction swab. The drying step includes suctioning moisture from the osteochondral defect through the suction swab or communicating a gas to the osteochondral defect through the suction swab.

4 Claims, 4 Drawing Sheets

(56) References Cited

U.S. PATENT DOCUMENTS

| | | | |
|---|---|---|---|
| 8,852,201 B2 | 10/2014 | Schmieding et al. | |
| 2011/0151405 A1* | 6/2011 | Dombrowski | A61M 1/008 433/96 |
| 2013/0338792 A1 | 12/2013 | Schmieding et al. | |
| 2015/0025311 A1* | 1/2015 | Kadan | A61B 1/015 600/104 |
| 2015/0165088 A1* | 6/2015 | Kajimoto | A61L 27/54 604/20 |

OTHER PUBLICATIONS

Kruse, Dustin et al. "Arthroscopic De Novo NT® Juvenile Allograft Cartilage Implantation in the Talus: A Case Presentation" The Journal of Foot & Ankle Surgery, 51 (2012) 218-221.*

Abrams, Geoffrey et al, BioCartilage: Background and Operative Technique, Per Tech Sports Med 21:116-124, 2013 Elsevier (Year: 2013).*

Kruse, Dustin et al. "Arthroscopic De Novo NT® Juvenile Allograft Cartilage Implantation in the Talus: A Case Presentation" The Journal of Foot & Ankle Surgery, 51 (2012) 218-221 (Year: 2012).*

Definition of common (Year: 2020).*

* cited by examiner

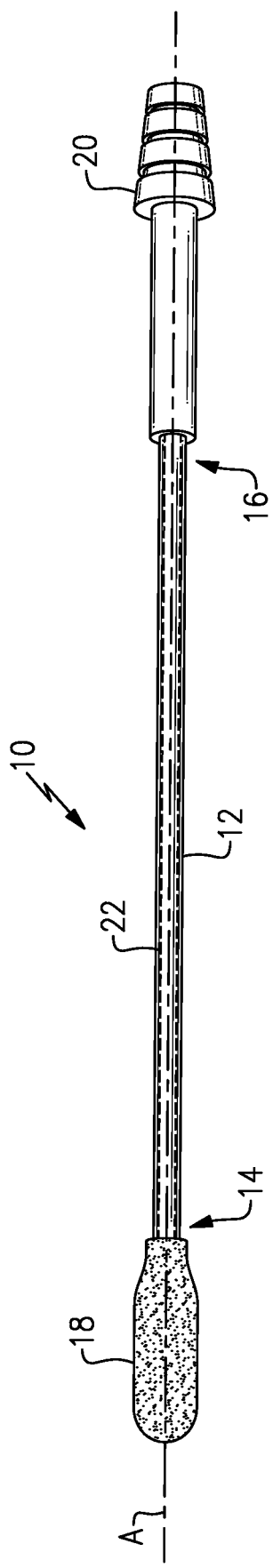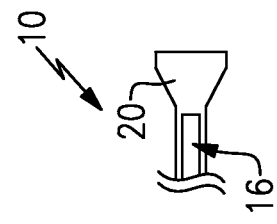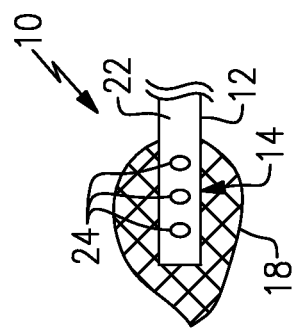

SUCTION SWAB FOR SURGICAL USE

BACKGROUND

This disclosure relates to a surgical method involving the use of a suction swab for drying an osteochondral defect.

Repetitive trauma to a joint, such as a knee, ankle, hip or shoulder joint, may cause osteochondral defects. Osteochondral defects are localized areas of damaged articular cartridge and adjacent subchondral bone of a joint. Osteochondral defects typically do not heal without treatment. For example, if not treated, the defect could further deteriorate the articular cartridge and underlying bone of the joint, and could result in relatively significant arthritic pain in some individuals.

Microfracture surgery is sometimes performed to treat osteochondral defects. During microfracture surgery, a surgeon creates small holes, or fractures, in the subchondral bone plate to generate bleeding from the bone. Blood and bone marrow may seep out of the holes and create a blood clot over the osteochondral defect. Stem cells from the bone marrow and the underlying subchondral bone interact with the blood clot and eventually form a fibrocartilagenous tissue network over the defect. In some microfracture surgeries, a repair material, such as an allograft mixture, is applied over the defect to augment the tissue network.

SUMMARY

A surgical method according to an exemplary aspect of the present disclosure includes, among other things, drying an osteochondral defect using a suction swab. The drying step includes suctioning moisture from the osteochondral defect through the suction swab or communicating a gas to the osteochondral defect through the suction swab.

In a further non-limiting embodiment of the foregoing method, the suction swab includes a swab tip received on a distal end of a tube and an adaptor received on a proximal end of the tube.

In a further non-limiting embodiment of either of the foregoing methods, the drying step includes suctioning the moisture through a swab tip of the suction swab, then through openings in a distal end of a tube of the suction swab, and then through a passage in the tube.

In a further non-limiting embodiment of any of the foregoing methods, the drying step includes communicating a gas through a passage in a tube of the suction swab, then through openings in a distal end of the tube, and then through a swab tip.

In a further non-limiting embodiment of any of the foregoing methods, the gas is an inert gas.

In a further non-limiting embodiment of any of the foregoing methods, the method includes creating a bleeding bone bed near the osteochondral defect prior to the drying step.

In a further non-limiting embodiment of any of the foregoing methods, the drying step is performed as part of an arthroscopic surgical procedure.

In a further non-limiting embodiment of any of the foregoing methods, the drying step is performed as part of an open surgical procedure.

In a further non-limiting embodiment of any of the foregoing methods, the moisture includes at least one of arthroscopy fluid, synovial fluid, blood or bone marrow.

In a further non-limiting embodiment of any of the foregoing methods, the drying step includes both suctioning moisture from the osteochondral defect through the suction swab and communicating the gas to the osteochondral defect through the suction swab.

A surgical method according to another exemplary aspect of the present disclosure includes, among other things, performing microfracture surgery to obtain a microfracture site and drying the microfracture site using a suction swab.

In a further non-limiting embodiment of the foregoing surgical method, the drying step includes suctioning moisture through the suction swab.

In a further non-limiting embodiment of either of the foregoing surgical methods, the drying step includes communicating a gas to the microfracture site through the suction swab.

In a further non-limiting embodiment of any of the foregoing methods, the microfracture site includes a plurality of perforations formed in subchondral bone near an osteochondral defect.

In a further non-limiting embodiment of any of the foregoing methods, the method includes applying a repair material over the microfracture site subsequent to the drying step.

A surgical method according to another exemplary aspect of the present disclosure includes, among other things, identifying an osteochondral defect in a joint space, creating a bleeding bone bed in bone near the osteochondral defect, drying the osteochondral defect with a suction swab, and delivering an allograft mixture over the osteochondral defect.

In a further non-limiting embodiment of the foregoing surgical method, the drying step includes suctioning moisture through the suction swab.

In a further non-limiting embodiment of either of the foregoing surgical methods, the drying step includes communicating a gas to the osteochondral defect through the suction swab.

In a further non-limiting embodiment of any of the foregoing surgical methods, the creating step includes performing a microfracture procedure in the bone.

In a further non-limiting embodiment of any of the foregoing surgical methods, the method includes applying a layer of fibrin over the allograft mixture.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 1 illustrates a suction swab.
FIG. 2 is a cross-section of a swab tip of a suction swab.
FIG. 3 illustrates an adaptor of a suction swab.

DETAILED DESCRIPTION

Figure 4:
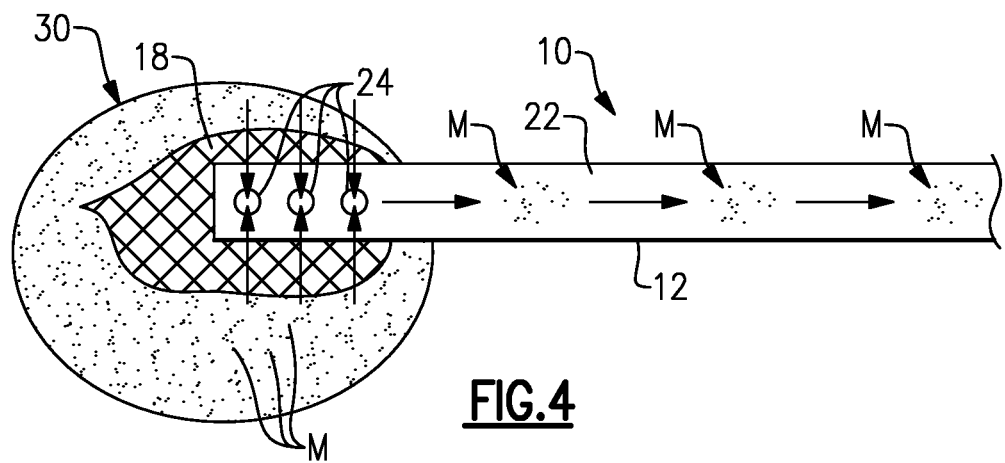
FIG. 4 schematically illustrates the use of a suction swab to dry an osteochondral defect by suctioning moisture from the defect.

This disclosure describes surgical methods for drying an osteochondral defect. The surgical methods include using a suction swab to dry the osteochondral defect. In some embodiments, the suction swab suctions moisture away from the osteochondral defect to dry the defect. In other embodiments, the suction swab communicates a gas to the osteochondral defect to dry the defect. The suction swab may be used to dry the osteochondral defect during microfracture surgeries or other osteochondral defect repairs. These and other features are described in greater detail in the following paragraphs of this disclosure.

FIGS. 1, 2 and 3 illustrate a suction swab 10. The suction swab 10 includes a tube 12 that extends along a longitudinal axis A between a distal end 14 and a proximal end 16. A swab tip 18 is disposed at the distal end 14, and an adaptor 20 is disposed at the proximal end 16. In one embodiment, the distal end 14 of the tube 12 is received within the swab tip 18, and the proximal end 16 of the tube 12 is received within the adaptor 20.

The tube 12 may be cannulated such that a passage 22 extends through its body. The passage 22 is disposed about the longitudinal axis A and may extend from the distal end 14 to the proximal end 16. The distal end 14 of the tube 12 may include a plurality of openings 24, or fenestrations, formed through the tube 12. The openings 24 are in fluid communication with the passage 22. In one non-limiting embodiment, the tube 12 is made of polystyrene. However, the tube 12 may be constructed of other similar materials within the scope of this disclosure.

The swab tip 18 is received over the distal end 14 of the tube 12. In one embodiment, the swab tip 18 is received over the distal end 14 of the tube 12 such that the openings 24 are positioned inside the swab tip 18. The swab tip 18 may be made of a wicking and/or moisture absorbing material. Cotton and foam are non-limiting examples of such materials. In one non-limiting embodiment, the swab tip 18 is capable of absorbing fluids including but not limited to arthroscopy fluid, synovial fluid, blood, bone marrow, etc.

The adaptor 20 of the suction swab 10 is configured for connection to a power device (not shown), such as a suction or gas device. In one embodiment, the adaptor 20 is a barbed adaptor (see FIG. 1). In another embodiment, the adaptor 20 is a luer type adaptor or a tapered adaptor (see FIG. 3). Other adaptor configurations are also contemplated.

The suction swab 10 can be used during surgical procedures to dry an osteochondral defect 30. The osteochondral defect 30 includes localized, damaged areas of articular cartilage and adjacent subchondral bone within a joint space, such as a knee, hip, ankle or shoulder joint space. The suction swab 10 can also be used to perform fluid management within the joint space during a surgical procedure.

For example, as shown in FIG. 4, moisture M (which could include arthroscopy fluid, synovial fluid, blood, bone marrow, etc.) that has pooled on the osteochondral defect 30 may be absorbed by the swab tip 18 of the suction swab 10. The moisture M is suctioned through the openings 24 of the tube 12 and then through the passage 22 to remove the moisture M and dry the osteochondral defect 30.

Figure 5:
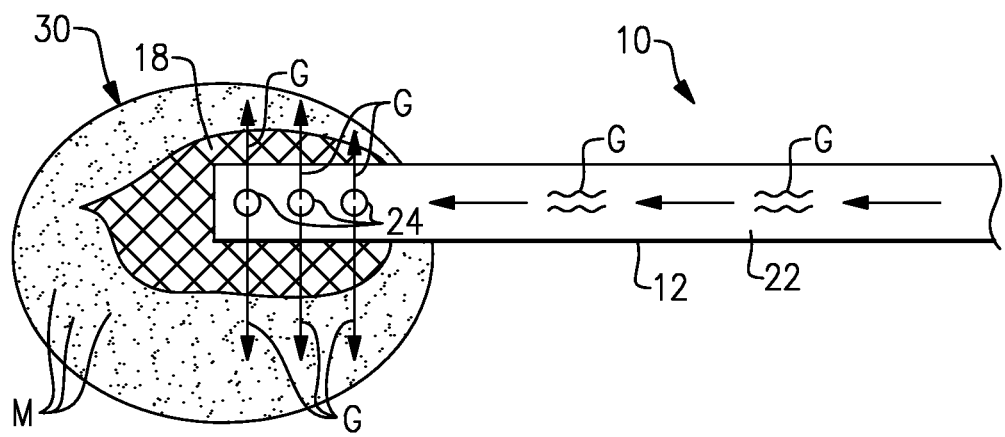
FIG. 5 schematically illustrates the use of a suction swab to dry an osteochondral defect by communicating a gas to the defect.

In an alternative embodiment, shown in FIG. 5, the suction swab 10 can be used to communicate a gas G to dry moisture M that has accumulated at the osteochondral defect 30. The gas G may be communicated through the passage 22 of the tube 12, then through the openings 24, and then through the swab tip 18 to dry the osteochondral defect 30. In one embodiment, the gas G is an inert gas, such as compressed air or nitrogen.

In yet another embodiment, the suction swab 10 can be used to dry the osteochondral defect 30 by both suctioning moisture from the osteochondral defect 30 and communicating the gas G to the osteochondral defect 30. FIGS. 4 and 5 are not necessarily drawn to scale and may be exaggerated to better illustrate the features of the suction swab 10.

FIGS. 6-11, with continued reference to FIGS. 1-5, schematically illustrate a method of using the suction swab 10 to prepare an osteochondral defect 30 for a subsequent surgical procedure. The method is illustrated and described as an arthroscopic method; however, the suction swab 10 could also be used in open procedures to dry defects.

In one non-limiting embodiment, the suction swab 10 is used to dry the osteochondral defect 30 to prepare a joint space 32 for receiving a repair material. Although the joint space 32 of FIGS. 6-11 is illustrated as a knee joint, the suction swab 10 of this disclosure could be used to dry osteochondral defects located anywhere within the human body.

Figure 6:
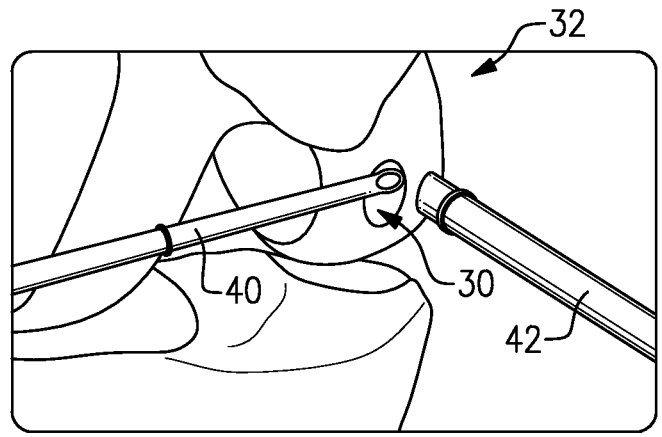
FIGS. 6, 7, 8, 9, 10 and 11 schematically illustrate a method of using a suction swab for preparing an osteochondral defect for a subsequent surgical procedure.

Referring first to FIG. 6, after the surgeon has identified the osteochondral defect 30 within the joint space 32, the osteochondral defect 30 is debrided to a stable border having perpendicular margins. Tools, such as a curette 40 and an elevator 42, can be used to create the vertical margins and debride the calcified cartilage layer at the base of the osteochondral defect 30.

Figure 7:
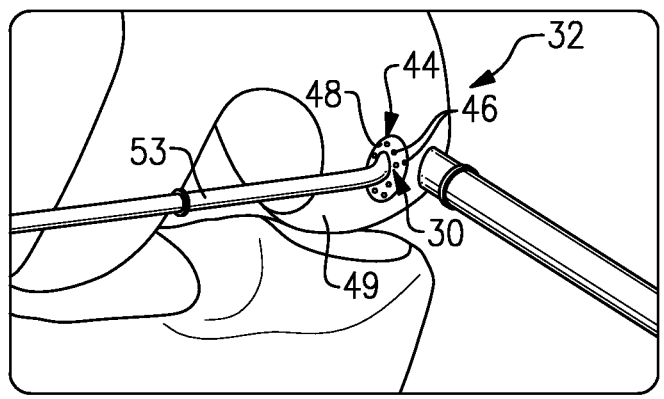

Next, as shown in FIG. 7, a microfracture procedure may be performed to obtain a microfracture site 44. During the microfracture surgery, the surgeon creates multiple perforations 46 in the subchondral bone 48 that extends beneath the articular cartilage 49 located near the osteochondral defect 30 of the joint space 32. In one embodiment, the microfracture procedure is performed using a tool 53, such as Arthrex's PowerPick™, to form the perforations 46 of the microfracture site 44. The formation of the perforations 46 creates a bleeding bone bed that stimulates bone marrow seepage into the microfracture site 44.

Figure 8:
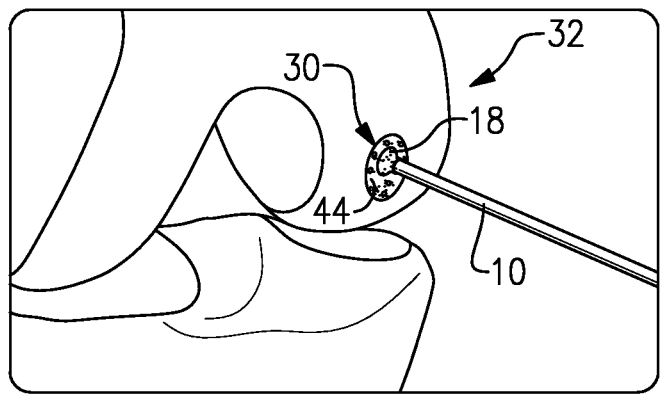

After creating the microfracture site 44, the osteochondral defect 30 is dried to remove excess moisture that could interfere with implantation of a repair material. As shown in FIG. 8, the osteochondral defect 30 is dried using the suction swab 10. The suction swab 10 is positioned within the joint space 32, and the swab tip 18 of the suction swab 10 may be positioned at the microfracture site 44 to begin wicking and/or absorbing any excess moisture. The moisture may be dried by suctioning the moisture out of the osteochondral defect 30 through the suction swab 10 or by introducing a gas to the osteochondral defect 30 through the suction swab 10.

It should be understood that the suction swab 10 of this disclosure is not limited to uses associated with microfracture surgeries. For example, in another non-limiting embodiment, the curette 40 shown in FIG. 6 could be used to create the bleeding bone bed within the joint space 32. The bleeding bone bed can then be dried as necessary using the suction swab 10 to prepare the osteochondral defect 30 for receiving a repair material or graft.

Figure 9:
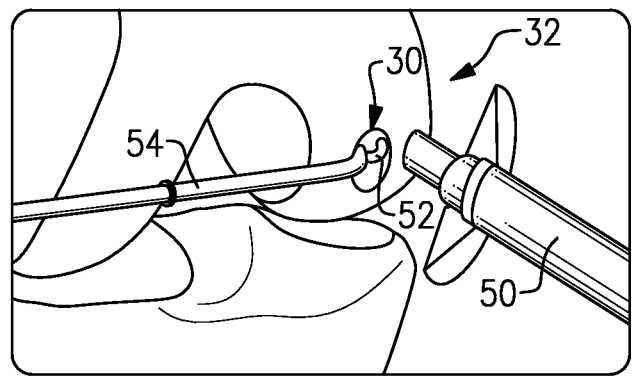

Referring to FIG. 9, a cannula 50 can be utilized in an arthroscopic portal that resides over the osteochondral defect 30. Distraction is applied with the cannula 50 to improve visualization of the osteochondral defect 30. A repair material 52 can then be applied over the osteochondral defect 30 using a delivery needle 54. In one non-limiting embodiment, the repair material 52 is an allograft mixture. The repair material 52 may include allograft cartilage in the form of micronized cartilage particulates which may be cartilage delivered in its native form, dehydrated via lyophilization, dehydrated via desiccation, or dehydrated by any other method. One non-limiting example of a suitable repair material 52 is Arthrex's BioCartilage®, which is a micronized cartilage matrix.

The repair material 52 serves as a scaffold over the osteochondral defect 30 and provides a tissue network that can potentially signal autologous cellular interactions and improve the degree and quality of tissue healing within the osteochondral defect 30. The repair material 52 can be smoothed within the osteochondral defect 30 so that it remains slightly recessed to the surrounding cartilage (see FIG. 10).

Figure 10:
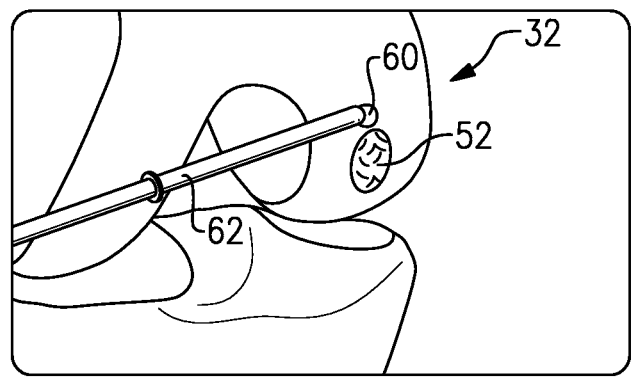
Figure 11:
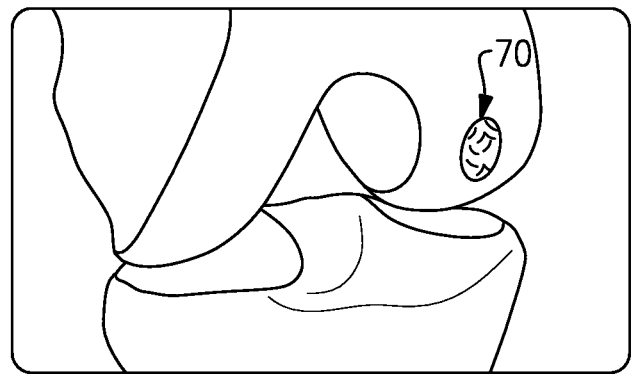

A layer of fibrin 60 may be applied over the repair material 52 via an applicator 62 (see FIG. 10). After letting the fibrin 60 and the repair material 52 sit for a predefined amount of time, such as approximately five minutes, the joint space 32 may be gently ranged before closure to assure adherence of the repair material 52 and completion of the final repair 70 (see FIG. 11).

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
debriding an osteochondral defect of a bone to a stable border having perpendicular margins,
wherein the debriding includes using a curette and an elevator to form the stable border;
creating a bleeding bone bed near the osteochondral defect of the bone;
drying the osteochondral defect with a suction swab, wherein drying the osteochondral defect includes:
suctioning moisture through a swab tip of the suction swab, then through a plurality of fenestrations formed through a distal end of a tube of the suction swab, and then through a passage in the tube; and
communicating a gas through the passage in the tube of the suction swab, then through the plurality of fenestrations, and then through the swab tip,
wherein the gas is nitrogen;
wherein the suctioning and the communicating occur at different times during the drying,
wherein the passage of the tube is a singular common passage of the tube;
inserting a cannula through an arthroscopic portal that resides over the osteochondral defect;
distracting the arthroscopic portal with the cannula to improve visualization of the osteochondral defect; and
delivering a micronized cartilage matrix scaffold over the osteochondral defect with a delivery needle.

2. The surgical method as recited in claim 1, wherein the swab tip is a cotton swab tip and the tube is made of polystyrene.

3. The surgical method as recited in claim 1, wherein the swab tip is a foam swab tip and the tube is made of polystyrene.

4. The method as recited in claim 1, wherein a proximal end of the tube is received within a barbed adaptor, and the barbed adapter includes a plurality of barbs.

\* \* \* \* \*